US00PP34477P2

(12) United States Plant Patent
Coakley

(10) Patent No.: US PP34,477 P2
(45) Date of Patent: Aug. 2, 2022

(54) ***DELPHINIUM* PLANT NAMED 'COADELSAM'**

(50) Latin Name: ***Delphinium* hybrid**
Varietal Denomination: 'COADELSAM'

(71) Applicant: Anthony Coakley, Glásgow (GB)

(72) Inventor: Anthony Coakley, Glásgow (GB)

( * ) Notice: Subject to any disclaimer, the term of this patent is extended or adjusted under 35 U.S.C. 154(b) by 0 days.

(21) Appl. No.: 17/803,154

(22) Filed: Mar. 8, 2022

(51) Int. Cl.
*A01H 5/02* (2018.01)
*A01H 6/72* (2018.01)

(52) U.S. Cl.
USPC ..... Plt./423

(58) Field of Classification Search
USPC ..... Plt./423
See application file for complete search history.

(56) References Cited

PUBLICATIONS https://www.gardenia.net/plant/delphinium-guardian-white. Retrieved from the Internet Apr. 26, 2022 (3 pages total).*

* cited by examiner

*Primary Examiner* — Susan McCormick Ewoldt
(74) *Attorney, Agent, or Firm* — Samuel R. McCoy, Jr.

(57) ABSTRACT

A new and distinct *Delphinium* hybrid plant named 'COADELSAM' which is characterized by basal foliage with compound terminal racemes held above the foliage with flowers held on long pedicels, flowers with an abundance of tepaloids, nearly-white tepals and tepaloids with violet-blue margins and a yellow-green central blotch near the apex, and the stability and uniformity of these traits through successive cycles of asexual propagation.

3 Drawing Sheets

Latin name of the genus and species: The Latin name of the genus and species of the novel variety disclosed herein is *Delphinium* hybrid.

Variety denomination: The inventive variety of *Delphinium* disclosed herein has been given the variety denomination 'COADELSAM'.

BACKGROUND OF THE INVENTION

Parentage: 'COADELSAM' is the result of a planned breeding program carried out in Blantyre, Scotland. The claimed plant is a seedling selection resulting from the controlled pollination of an unnamed *Delphinium* hybrid plant, the seed parent, with a second unnamed *Delphinium* hybrid plant, the pollen parent, in the summer of 2013. Both parents were developed and are owned by the inventor and were never released or patented. In the summer of 2014, one plant was observed to exhibit uniquely colored flowers with a high tepaloid count and was isolated for further evaluation in order to confirm the distinctness and stability of the characteristics first observed. Upon confirmation of distinctness and stability, 'COADELSAM' was selected for commercialization.

Asexual Reproduction: In the spring of 2015, 'COADELSAM' was first asexually reproduced in Blantyre, Scotland by way of softwood stem cuttings. The claimed plant was found to asexually reproduce in uniform and stable manner and six successive cycles of vegetative propagation have proven to be true to type.

SUMMARY OF THE INVENTION

The following characteristics have been repeatedly observed and represent the distinguishing characteristics of the new *Delphinium* plant, 'COADELSAM'. These traits, in combination, distinguish 'COADELSAM' as a new and distinct cultivar.

1. 'COADELSAM' exhibits basal foliage with a compound terminal raceme held above the foliage; and
2. 'COADELSAM' exhibits flowers that are held on long pedicels along the raceme; and
3. 'COADELSAM' exhibits an abundance of tepaloids; and
4. 'COADELSAM' exhibits flowers with multiple whorls of tightly held tepaloids at the center of the perianth, somewhat more relaxed tepaloids towards the outer whorls of the perianth, and an outer whorl of loosely held tepals; and
5. 'COADELSAM' exhibits nearly-white tepals and tepaloids with a yellow-green central blotch near the apex; and
6. 'COADELSAM' exhibits tepal and tepaloid margins that are suffused with a mixture of violet-blue.

BOTANICAL DESCRIPTION OF THE PLANT

Figure 1:
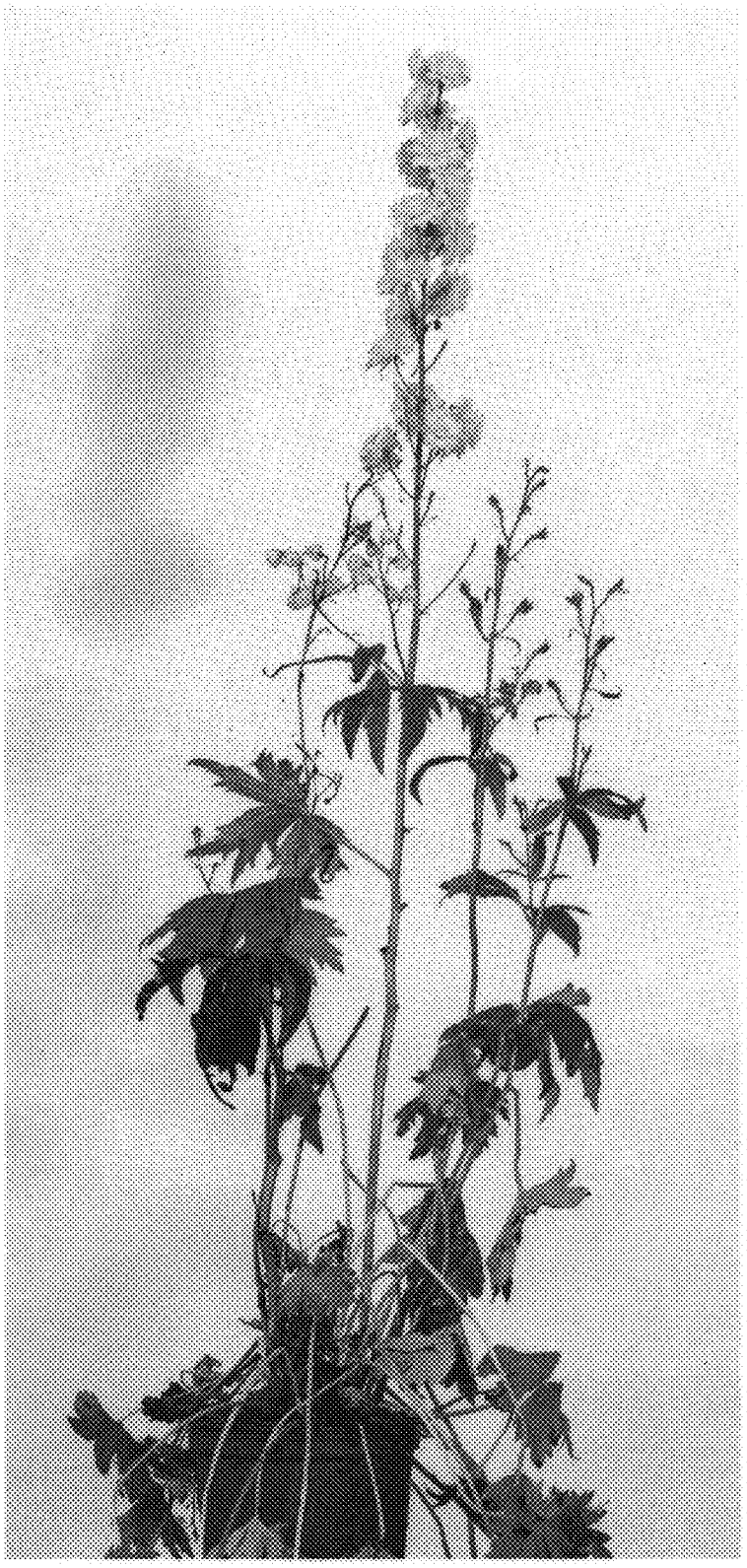
FIG. 1 illustrates, as nearly true as it is reasonably possible to make the same in color photographs of this type, a 12-month-old 'COADELSAM' plant, grown outdoors in Glasgow, Scotland and subsequently transferred to 17 cm nursery containers for the purpose of photography.
Figure 2:
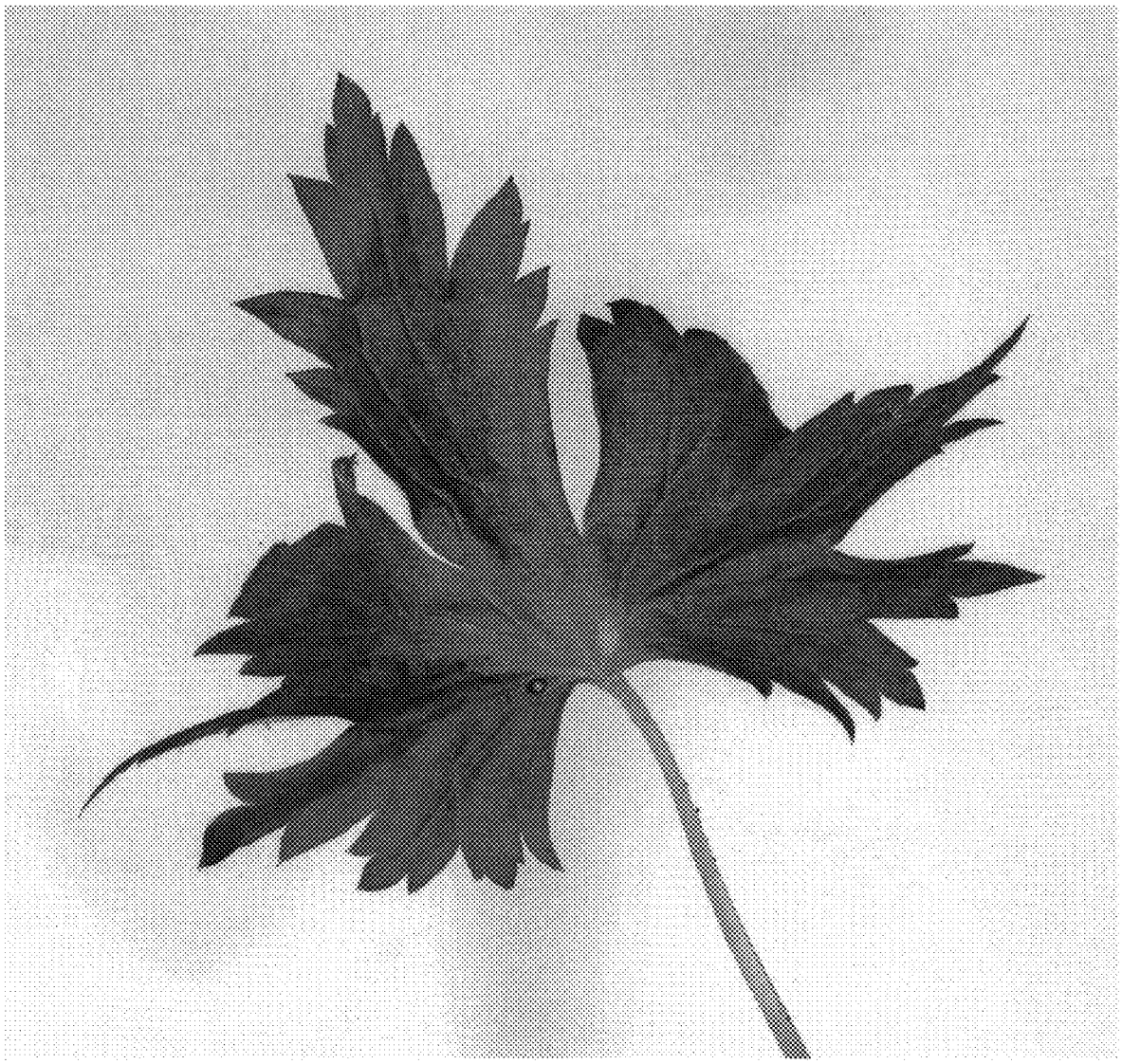
FIG. 2 illustrates, as nearly true as it is reasonably possible to make the same in color photographs of this type, the foliage of 'COADELSAM'.
Figure 3:
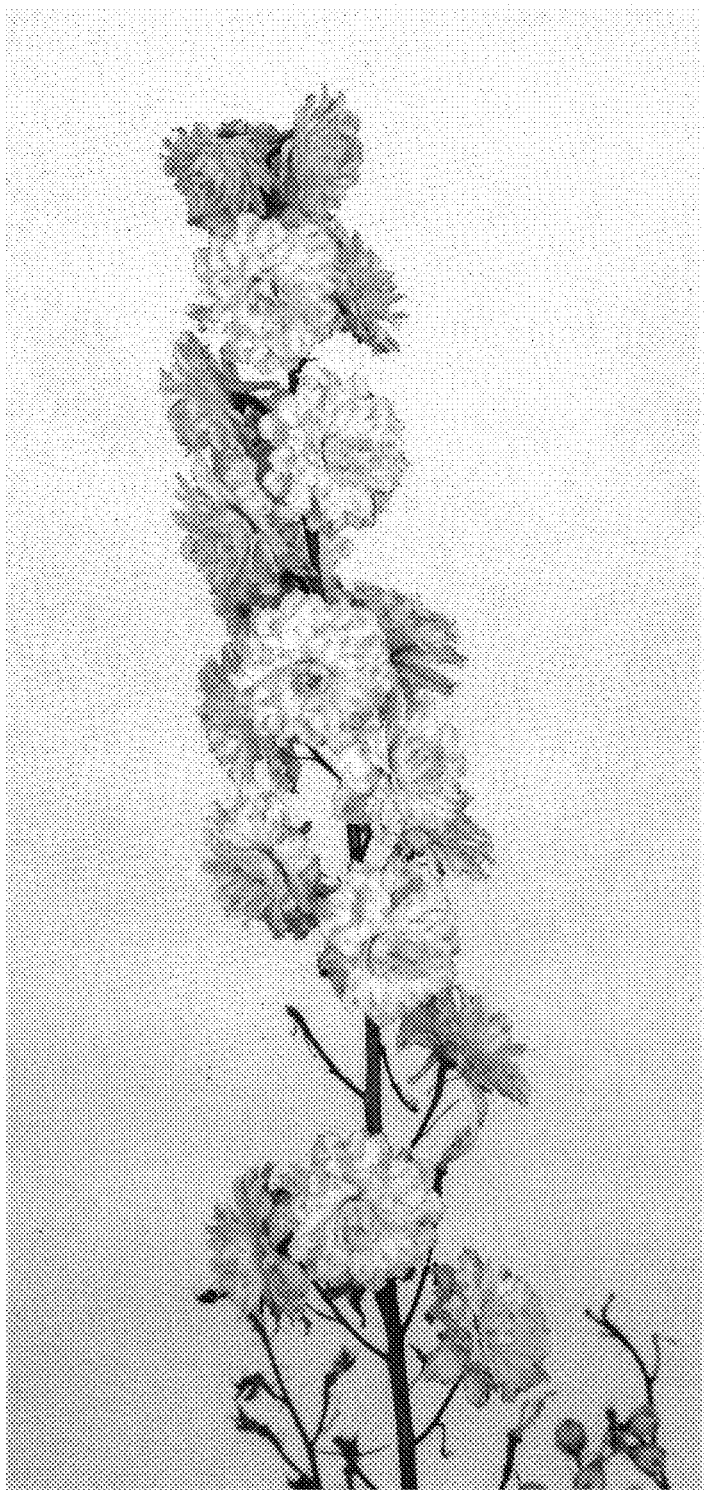
FIG. 3 illustrates, as nearly true as it is reasonably possible to make the same in color photographs of this type, the inflorescence of 'COADELSAM'.

The following is a detailed botanical description of a new and distinct *Delphinium* plant known as 'COADELSAM'.

Plant observations were made on a 12-month-old plant growing in Glasgow, Scotland. The observed plant was field-grown in full exposure to natural sunlight, maintained with organic fertilizer and overhead irrigation. Chemical control of powdery mildew was utilized in production, but no other pest or pathogen countermeasures were employed. For the purposes of these observations, the observed plant was harvested from the field and potted into a 17 cm nursery container. Observation data was recorded in October of 2021.

Those skilled in the art will appreciate that certain characteristics will vary with older or, conversely, younger plants. 'COADELSAM' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, Sixth Edition except where common terms of color are used.

A botanical description of 'COADELSAM' and comparisons with the parents and most similar commercial cultivar are provided below.

General plant description:

*Plant habit*.—Herbaceous perennial plant with basal foliage and branched flowering stems, bearing flowers arranged on terminal racemes held above the foliage.

*Plant profile*.—Narrow ovate to ovate.

*Height*.—55.7 cm to the top of the foliar plane; 101.4 cm to the top of the floral plane.

*Spread*.—48.0 cm.

*Plant vigor*.—Moderately vigorous to highly vigorous.

*Growth rate*.—Moderately-fast growing.

*Propagation*.—Method — Softwood stem cuttings. Time to initiate rooting — 6 weeks at an average ambient temperature of 15 degrees Celsius. Time to produce flowering plant from rooted cutting — Approximately 6 months in an 11 cm container.

*Pest resistance and susceptibility*.—Not any more or less susceptible to pests or diseases known to effect *Delphinium* sp.

*Environmental tolerances*.—Adapt to, at least, USDA Zones 5 to 9 and temperatures ranging from minus 23 degrees Celsius to 35 degrees Celsius; moderate tolerance to rain; low tolerance to wind.

Root system:

*Description*.—A moderately dense network of relatively shallow thin, fibrous feeder roots and deeper thick anchor roots.

Stems:

*Branching habit*.—No vegetative branches are present, however branched flowering stems are present.

*Flowering stem*.—Quantity — 5 stems per plant, as observed. Attitude — Erect; near vertical. Aspect — Generally rounded; slightly angular. Strength — Strong. Length — 46.1 cm. Diameter — 0.7 cm. Internode length — 6.1 cm; varying from 1.6 cm to 19.0 cm. Texture — Moderately pubescent; short, soft hairs with an average length of 0.2 cm and colored greyed-white, nearest to RHS 156D. Luster — Matte, due to the presence of epicuticular wax. Color, developing stems — Yellow-green, nearest to in between RHS 146C and 146D. Color, mature stems — Yellow-green, nearest to RHS 146C, and covered with an epicuticular wax which is colored yellow-green, nearest to RHS 148D. Color at the internodes — Yellow-green, nearest to RHS 146C, and covered with an epicuticular wax which is colored yellow-green, nearest to RHS 148D.

Foliage:

*Arrangement*.—Alternate.

*Attachment*.—Petiolate.

*Division*.—Simple.

*Quantity*.—8 stem leaves.

*Shape*.—Palmate with a broad reniform outline; lobed.

*Lobes*.—Depth of sinuses — Moderately deep to deep. Sinus orientation — Convergent.

*Aspect*.—Slightly convex.

*Attitude*.—Outward.

*Length*.—13.6 cm.

*Width*.—17.2 cm.

*Apex*.—Narrowly acute.

*Base*.—Hastate; lobes free.

*Margins*.—Coarsely serrate; moderately pubescent.

*Texture and pubescence, adaxial surface*.—Smooth and sparsely pubescent with very short, soft hairs with an average length of 0.5 cm and colored white, nearest to RHS N155A.

*Texture and pubescence, abaxial surface*.—Smooth and moderately covered with very short, soft hairs with an average length of 0.15 cm and greyed-colored white, nearest to RHS 156D.

*Luster, adaxial surface*.—Matte.

*Luster, abaxial surface*.—Matte.

*Color*.—Juvenile foliage color, adaxial surface — Green, nearest to a mixture of RHS 137C and 143A. Juvenile foliage color, abaxial surface — Yellow-green, nearest to a mixture of RHS 146B and 147B. Mature leaf color, adaxial surface — Green, nearest to RHS NN137A. Mature leaf color, abaxial surface — Yellow-green, nearest to a mixture of RHS 146B and 147B.

*Venation*.—Type — Laciniate. Vein color, adaxial surface — Yellow-green, nearest to RHS 144A. Vein color, abaxial surface — Yellow-green, nearest to a mixture of RHS 146A and 146B.

*Petiole*.—Length — 24.7 cm. Diameter — Petioles are flattened; 0.35 cm tall and 0.3 cm wide. Strength — Very strong. Texture, adaxial and abaxial surfaces — Smooth and moderately covered with very short, soft hairs with an average length of 0.15 cm and colored white, nearest to RHS NN155A. Luster, adaxial and abaxial surfaces — Moderately glossy. Color, adaxial surface — Yellow-green, nearest to RHS 144A. Color, abaxial surface — Yellow-green, nearest to RHS 144A.

*Stipules*.—None.

Inflorescence:

*Inflorescence type*.—Compound terminal raceme with a central, primary raceme and lateral racemes.

*Natural flowering season*.—Late summer in Glasgow, Scotland.

*Time to flower or response time*.—Approximately 9 months.

*Height*.—The entire compound raceme is 54.4 cm high, from the lowest branching of the peduncle to the apex of the inflorescence. The primary, central raceme is 44.4 cm tall.

*Diameter*.—The entire compound raceme is 28.0 cm in diameter; the primary, central raceme is 9.4 cm in diameter.

*Quantity of flowers per inflorescence*.—50 on the entire compound raceme; 30 on the primary raceme.

*Quantity of flower buds per plant*.—Average of 170.

*Quantity of open flowers per plant*.—Average of 30.

*Peduncle*.—Length — Approximately 50.8 cm. Diameter — Approximately 0.4 cm. Attitude — Erect, in an average angle of 0 degrees to the main stem. Strength — Strong. Texture — Smooth, glabrous, and glaucous. Luster — Matte. Color — Yellow-green, nearest to RHS 146A; epicuticular wax is yellow-green, nearest to RHS N148B.

*Bracts*.—Quantity — Two bracts are present at the base of each individual flower. Arrangement — Opposite. Shape — Linear. Length — 1.0 cm, on average. Width — 0.08 cm, on average. Apex — Narrowly acute. Base — Cuneate. Margin — Entire. Texture — Smooth and sparsely covered with short, soft hairs with an average length of 0.05 cm and colored white, nearest to RHS N155A. Color, adaxial and abaxial surfaces — Yellow-green, nearest to a mixture of RHS 146B and 146C.

Flower bud:

*Shape*.—Broad obovate, excluding the floral spur.

*Length*.—Average of 1.8 cm.

*Height*.—1.1 cm.

*Width*.—1.0 cm.

*Texture*.—Smooth and moderately covered with short, soft hairs with an average length of 0.075 cm and colored white, nearest to RHS N155A.

*Luster*.—Matte.

*Color, upper surface*.—Greyed-white, nearest to RHS 156C, and suffused with yellow-green at the apex, nearest to RHS 146B.

*Color, lower surface*.—White, nearest to RHS NN155B, and suffused with yellow-green at the apex, nearest to RHS 146B.

*Color, spur*.—Greyed-white, nearest to RHS 156C.

Flower:

*Type and form*.—Rotate; double.

*Aspect*.—Outward.

*Flowering habit*.—Freely flowering.

*Flower longevity on plant*.—Approximately 10 days.

*Longevity of cut flowers*.—Approximately 10 days.

*Persistent or self-cleaning*.—Self-cleaning.

*Fragrance*.—Non-fragrant.

*Height*.—Average of 4.1 cm.

*Width*.—Average of 4.2 cm.

*Depth*.—Average of 2.7 cm.

*Perianth*.—No distinct petals and sepals, only tepals and tepaloids are present. Tepals — Quantity — 5 unfused tepals; one dorsal, two lateral, and two lower tepals. Arrangement — Rotate; single whorl. Attitude — Relaxed. Aspect — Moderately concave. Length — Dorsal tepal — 1.9 cm. Lateral tepals — 2.0 cm. Lower tepals — 2.0 cm. Width — Dorsal tepal — 1.35 cm. Lateral tepals — 1.3 cm. Lower tepals — 1.1 cm. Shape — Dorsal tepal is elliptic to broad obovate; lateral tepals are broad obovate. Apex — All tepals are broad apiculate. Base — All tepals are broad cuneate. Margin — All tepals are entire and either exhibit no undulation or very slight undulation. Texture and pubescence of the upper surface — All tepals are glabrous, slightly velvety, and matte. Texture and pubescence of the lower surface — All tepals are smooth and moderately pubescent with very short, soft hairs with an average length of 0.075 cm and colored white, nearest to RHS N155A. Luster of the upper surface — All tepals are matte. Luster of the lower surface — All tepals are matte. Color when opening, upper surface — Dorsal tepal — Green-white, nearest to RHS 157D, and suffused with a darker shade of green-white, nearest to RHS 157A; apex and base are yellow-green, nearest to RHS 146C. Margins are narrowly and very lightly suffused with violet-blue, nearest to RHS 98C. Lateral tepals — Nearest to a mixture of white and greyed-white, RHS N155B and 156D; apex and base are yellow-green, nearest to RHS 146C. Margins are narrowly and very lightly suffused with violet-blue, nearest to RHS 98C. Lower tepals — Nearest to a mixture of white and greyed-white, RHS N155B and 156D; apex and base are yellow-green, nearest to RHS 146C. Margins are narrowly and very lightly suffused with violet-blue, nearest to RHS 98C. Color when opening, lower surface — Dorsal tepal — Greyed-white, nearest to RHS 156A; apex and base are yellow-green, nearest to RHS 146C. Margins are narrowly and very lightly suffused with violet-blue, nearest to RHS 98C. Lateral tepals — Nearest to a mixture of white and greyed-white, RHS N155B and 156D; apex and base are yellow-green, nearest to RHS 146B. Margins are narrowly and very lightly suffused with violet-blue, nearest to RHS 98C. Lower tepals — Nearest to a mixture of white and greyed-white, RHS N155B and 156D; apex and base are yellow-green, nearest to RHS 146B. Margins are narrowly and very lightly suffused with violet-blue, nearest to RHS 98C. Color when fully opened, upper surface — Dorsal tepal — Nearest to a mixture of white and grey, RHS N155A and 201D; a yellow-green central blotch is present near the apex and base, nearest to RHS 146D. Margins are narrowly and very lightly suffused with violet-blue, nearest to RHS 98C. Tepals do not fade with age. Lateral tepals — White, nearest to RHS N155A, and suffused with grey, nearest to RHS 201D; a yellow-green central blotch is present near the apex and base, nearest to in between RHS 146C and 146D. Margins are narrowly and very lightly suffused with violet-blue, nearest to RHS 98C. Tepals do not fade with age. Lower tepals — White, nearest to RHS N155A, and suffused with grey, nearest to RHS 201D; a yellow-green central blotch is present near the apex and base, nearest to in between RHS 146C and 146D. Margins are narrowly and very lightly suffused with violet-blue, nearest to RHS 98C. Tepals do not fade with age. Color when fully opened, lower surface — Dorsal tepal — Grey, nearest to RHS 201D; a yellow-green central blotch is present near the apex and base, nearest to RHS 146C. Margins are narrowly and very lightly suffused with violet-blue, nearest to RHS 98C. Tepals do not fade with age. Lateral tepals — White, nearest to a mixture of RHS N155A and N155B, with a grey central band, nearest to RHS 201D; a yellow-green central blotch is present near the apex and base, nearest to RHS 146C. Margins are narrowly and very lightly suffused with violet-blue, nearest to RHS 98C. Tepals do not fade with age. Lower tepals — White, nearest to a mixture of RHS N155A and N155B, with a grey central band, nearest to RHS 201D; a yellow-green central blotch is present near the apex and base, nearest to RHS 146C. Margins are narrowly and very lightly suffused with violet-blue, nearest to RHS 98C. Tepals do not fade with age. Tepal venation color — Fully opened, upper surface — No visible venation. Fully opened, lower surface — Grey, nearest to a mixture of RHS 201C and 201D. Tepaloids — Arrangement — Rotate; the unfused tepaloids are relatively tightly-held in 5 whorls. Attitude — Inner tepaloids are erect; outer tepaloids are somewhat relaxed. Aspect — Inner tepaloids are concave and reflexed; outer tepaloids are slightly concaved and reflexed. Quantity — 50. Length — 1.95 cm. Width — 0.9 cm. Shape — Narrowly obovate to obovate. Apex — Broad acute. Base — Cuneate. Margin — Entire; no undulation to slight undulation. Texture, luster and pubescence of the inner surface — Moderately velvety, glabrous and matte. Texture, luster and pubescence of the outer surface — Moderately velvety, glabrous and matte. Color when opening, upper surface — White, nearest to RHS NN155D, and suffused with green-white, nearest to RHS 157C; a yellow-green central blotch is present near the apex and base, nearest to in between RHS 145A and 145B. Margins are narrowly and very lightly suffused with violet-blue, nearest to RHS 98C. Color when opening, lower surface — White, nearest to RHS NN155D, and suffused with green-white, nearest to RHS 157C; a yellow-green central blotch is present near the apex and base, nearest to in between RHS 145A and 145B. Margins are narrowly and very lightly suffused with violet-blue, nearest to RHS 98C. Color when fully opened, upper surface — White, nearest to RHS NN155D, and suffused with green-white, nearest to RHS 157C; a yellow-green central blotch is present near the apex and base, nearest to RHS 145A. Margins are narrowly and very lightly suffused with violet-blue, nearest to RHS 98C. Color when fully opened, lower surface — White, nearest to RHS NN155D, and suffused with green-white, nearest to RHS 157C; a yellow-green central blotch is present near the apex and base, nearest to RHS 145A. Margins are narrowly and very lightly suffused with violet-blue, nearest to RHS 98C. Tepaloid venation color when fully opened, inner surface — Yellow-green, nearest to a mixture of RHS 145A, 145B and 145C. Tepaloid venation color when fully opened, outer surface — Yellow-green, nearest to a mixture of RHS 145A, 145B and 145C. Pedicels — Length — 3.5 cm. Diameter — 0.125 cm. Angle — Average angle to peduncle axis is approximately 35 degrees. Strength — Moderately strong. Texture — Smooth and glabrous with the exception of the distal end which is sparsely to moderately covered with very short, soft hairs with an average length of 0.05 cm and colored white, nearest to RHS N155A. Luster — Glossy. Color — Yellow-green, nearest RHS 146A. Spurs — Quantity — One dorsal tepal spur present. Length — 1.0 cm. Diameter — 0.25 cm. Shape — Oblong: Apex — Obtuse. Base — Broad cuneate. Texture — Moderately rugose and glabrous. Luster — Moderately glossy. Color — Yellow-green, nearest to in between RHS N148C and N148D.

Reproductive organs:

*Stamens*.—All stamens are reduced to tepaloid staminodes.

*Pistil*.—Quantity — 2. Length — 0.3 cm. Style — Length — 0.25 cm. Color — Greyed-purple, nearest to RHS 186C. Stigma — Shape — Pointed. Length — 0.05 cm. Diameter — 0.025 cm. Color — Greyed-purple, nearest to RHS 186C. Ovary Color — The undeveloped ovary is colored yellow-green, nearest to RHS 144C.

Fruit and seed: No fruiting has been observed.

Comparison With the Parent Plant

Plants of the new cultivar 'COADELSAM' differ from the seed parent, an unnamed *Delphinium* hybrid (not patented), by the characteristics described in Table 1.

TABLE 1

| Characteristic | 'COADELSAM' | The seed parent. |
|---|---|---|
| Quantity of tepaloids. | More than the seed parent. | Fewer than 'COADELSAM'. |

Plants of the new cultivar 'COADELSAM' differ from the pollen parent, an unnamed *Delphinium* hybrid (not patented), by the characteristics described in Table 2.

TABLE 2

| Characteristic | 'COADELSAM' | The pollen parent. |
|---|---|---|
| Quantity of tepaloids. | More than the pollen parent. | Fewer than 'COADELSAM'. |

Comparison With the Most Similar *Delphinium* Cultivar Known to the Inventor

Plants of the new cultivar 'COADELSAM' are most similar to the commercial cultivar, *Delphinium* hybrid 'COADELCHA' (U.S. Plant Pat. No. 27,735). A comparison of 'COADELSAM' with *Delphinium* 'COADELCHA' is described in Table 3.

TABLE 3

| Characteristic | 'COADELSAM' | 'COADELCHA' |
|---|---|---|
| Length of the inflorescence. | Longer than 'COADELCHA'. | Shorter than 'COADELSAM'. |
| General coloration of the flowers. | Nearly-white tepals and tepaloids with violet-blue margins and a yellow-green central blotch. | A combination of dark purple and blue. |

That which is claimed is:

1. A new and distinct variety of *Delphinium* hybrid plant named 'COADELSAM', substantially as described and illustrated herein.

* * * * *